United States Patent [19]

Königstein et al.

[11] 3,963,674

[45] June 15, 1976

[54] PROCESS FOR THE PRODUCTION OF HALOGENATED CARBOXYLIC ACID AMIDES

[75] Inventors: Otto Königstein; Herbert Jenkner, both of Cologne, Germany

[73] Assignee: Chemische Fabrik Kalk GmbH, Germany

[22] Filed: Mar. 7, 1975

[21] Appl. No.: 556,429

[30] Foreign Application Priority Data

Mar. 13, 1974 Germany............................ 2411904

[52] U.S. Cl.......................................... 260/561 HL
[51] Int. Cl.$^2$...................................... C07C 103/02
[58] Field of Search............................. 260/561 HL

[56] References Cited
OTHER PUBLICATIONS

Chem. Abs. 66, 116621.
Chem. Abs. 68, 59672.

*Primary Examiner*—C. Davis
*Attorney, Agent, or Firm*—Laurence, Stokes & Neilan

[57] ABSTRACT

A process for the production of halogenated carboxylic acid amides wherein an amide of the unsaturated aliphatic carboxylic acid is reacted with an anhydrous hydrogen halide and an epoxide compound is added to the reaction mixture and after cooling, the precipitated halogenated carboxylic acid amide is separated.

9 Claims, No Drawings

PROCESS FOR THE PRODUCTION OF HALOGENATED CARBOXYLIC ACID AMIDES

Various processes for the production of halogenated carboxylic acid amides have already been known. Thus, for example, C. S. Hamilton and C. L. Simpson in the Journal of the American Chemical Society 51 (1929) 3 158 described the conversion of 3-bromopropionyl chloride with concentrated ammonia at a temperature of − 10°C, in which case 3-bromopropionic amide is obtained. According to this citation N-phenyl-β-aminopropionamide-4-arsonic acid is prepared by dissolving sodium p-arsanilate in sodium hydroxide and reacting this with 3-bromopropionic amide (or with 3-iodopropionicamide) under refluxing conditions. The product is stated to have use in treating trypanosomal infections. Related compounds may also be prepared by employing different amino arylarsinic acid reactants. Another process wherein 3-bromopropionic amide can be produced is given by H. W. Johnson and D. E. Bublitz in J. Amer. Chem. Soc. 79 (1957) 753 to 754. In this case, first of all N-bromosuccinic imide dissolved in chloroform is rearranged in the presence of allyl halides and benzoyl peroxide to 3-bromopropionylisocyanate. The latter can be converted further by treatment with water and with carbon dioxide elimination into 3-bromopropionic amide.

These processes which had been tried hitherto only at the laboratory level always started out from organic compounds already halogenated. Therefore in the case of an industrial application, it would be necessary in every case first of all to produce the halogenated organic compound, such as for example, 3-bromopropionyl chloride or N-bromosuccinic imide, separately in several processing steps. The real production process for the halogenated carboxylic acid amide would then be carried out only subsequently thereto. Such a method of operation is however very expensive technically speaking.

Therefore, a process was sought according to which it would be possible to process halogenated carboxylic acid amides from technically easily accessible substances in a simple manner.

A process for the production of halogenated carboxylic acid amides was found. This process is distinguished by the fact, that an amide of the unsaturated aliphatic carboxylic acid is reacted with an anhydrous hydrogen halide, whereupon an epoxide compound is added to the reaction mixture and from that, after cooling, the precipitated halogenated carboxylic acid amide is separated.

In order to carry out the process according to the invention, the amide of an unsaturated aliphatic carboxylic acid is first of all dissolved in an organic solvent. Carboxylic acid esters, such as for example, methyl acetate or ethyl acetate, are particularly suited as solvents. Halogenated hydrocarbons, such as for example, chloroform, carbon tetrachloride or CCl$_2$R-CCl$_2$R, can likewise be used. At the same time, it is not absolutely necessary that the amide of the unsaturated aliphatic carboxylic acid be completely dissolved in the solvent; a suspension of the amide in the pertinent solvent can be used just as well.

Anhydrous hydrogen halide, such as hydrogen bromide, hydrogen chloride or hydrogen fluoride, is introduced into this solution or suspension at ambient temperature. At the same time, in the case of the use of acrylic amide as a starting substance and hydrogen bromide, the following reaction takes place:

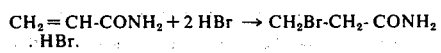

The quantity of the hydrogen halide introduced should be in a proportion of 2 to 2.1 moles for 1 mole of the amide.

Since the reaction takes an exothermal course, the temperature of the reaction mixture rises after a short time. It is then held at a value between 20° and 50°C by a suitable cooling arrangement. First of all an addition-compound from halogenated carboxylic acid amide and hydrogen halide is formed. In order to split this addition-compound into halogenated carboxylic acid amide and hydrogen halide, an alkylene oxide or an epihalogen compound is added to the reaction mixture while maintaining the reaction temperature. At the same time one can use as alkylene oxide, for example, ethylene oxide, propylene oxide or butylene oxide. As an epihalogen compound, epichlorohydrine or epibromohydrine can be used. Apparently, and in continuation of the previously mentioned example, the following reaction takes its course hereby:

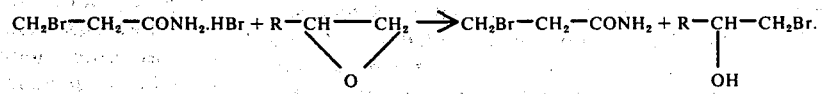

Advantageously the alkylene oxide or the epihalogen compound are inserted into the reaction mix in stoichiometric quantity, related to the amide of the unsaturated aliphatic carboxylic acid used, possibly with an excess of 5 to 10%.

The end of the conversion can be recognized from the fact that the reaction mixture which at first is acid, reacts neutrally. The halogenated carboxylic acid amide, which had become free during the reaction, is separated in the form of fine crystals. In order to achieve a favorable yield, the reaction mix is cooled to a temperature between 10° and 20°C, and the solid end product is separated by filtration, centrifuging or some other suitable measure from the mother liquid. After drying in the vacuum, a pure, colorless halogenated carboxylic acid amide is obtained as the end product at a theoretical yield of at least 70%. Possibly the yield can still be increased by concentration of the mother liquid. Whenever carboxylic acid esters are used as solvents, then alkyl bromides are formed as secondary products, for example methyl bromide or ethyl bromide.

Of the various halogenated carboxylic acid amides that can be produced according to the process of the invention, the 3-bromopropionic amide is of particular interest. Just like other additives of the 3-bromopropionic acid, it represents an important starting product for the synthesis of various organic products, especially of pharmacological agents and pesticides.

A few examples are set forth to explain the process of the invention in more detail:

EXAMPLE 1

355g of acrylic amide, which are suspended in 370g of methyl acetate, are poured into a glass reaction vessel of 2 liters content. This vessel is provided with a thermometer, an agitator, gas introducing tube and outside cooling. Into this suspension 810g of hydrogen bromide are introduced at ambient temperature in the course of 5 hours. After a brief introduction time, the temperature of the reaction mix begins to rise. The temperature is held to 50°C by outside cooling. After completion of the addition of hydrogen bromide and in the course of another 3 hours, 319g of propylene oxide are added drop by drop, with the temperature still kept at 50°C by the cooling. After the conversion has been completed, the reaction mix is cooled to 15°C and is filtered subsequently. The crystals of 3-bromopropionic amide separated thereby are washed with a little methyl acetate on the filter and are subsequently dried at 50°C. 532g of 3-bromopropionic amide with a melting point between 112° and 115°C are thus obtained. This corresponds to 70% of the theory related to acrylic amide.

EXAMPLE 2

In the apparatus described in Example 1, 355g of acrylic amide are suspended in 370g of methyl acetate and are reacted under the conditions stated in Example 1 with 810g of hydrogen bromide. At the completion of the addition of hydrogen bromide and in the course of 5 hours, 220g of ethylene oxide are introduced with the temperature still kept at 50°C by cooling. After completed reaction, the reaction mix is cooled to 15°C and is filtered subsequently. The crystals of 3-bromopropionic amide separated thereby are dried at 50°C. 548g of 3-bromopropionic amide with a melting point between 114° and 115°C are obtained, that corresponds to 72% of the theory related to acrylic amide.

EXAMPLE 3

In the apparatus described in Example 1, 2322g of acrylic amide are suspended in 2430g of methyl acetate and 5322g of hydrogen bromide are introduced into this suspension in the course of 13 hours, with the temperature of the reaction mix held below 35°C by cooling. Then the outlet of the cooler is connected with a cooling trap and subsequently during the course of 3 hours, 1870g of propylene oxide are added drop by drop. The methyl bromide formed thereby is separated in the cooling trap.

After completion of the propylene oxide addition, the reaction mix is cooled to a temperature of 15°C and is then filtered. The crystals of 3-bromopropionic amide obtained thereby are washed and dried as in Example 1. 3574g of 3-bromopropionic amide are obtained corresponding to a yield of 71% of the theory. 500g of methyl bromide is obtained in the cooling trap as a side product.

Whenever instead of 5322g of hydrogen bromide a quantity of 5818g is used and subsequently 2212 g of propylene oxide are added drop by drop, then the yield of 3-bromopropionic amide is increased to 4339g, corresponding to 86.4% of the theory.

EXAMPLE 4

710g of acrylic amide are suspended in 720g of ethyl acetate according to the same method of operation as in Example 1 and they are reacted with 1620g of hydrogen bromide and subsequently with 627g of propylene oxide. After filtration, washing and drying of the residue, 1134g of 3-bromopropionic amide are obtained, corresponding to 74% of the theory. From the mother liquid 180g of ethyl bromide are obtained as a side product by fractionated distillation.

EXAMPLE 5

85g of methacrylic amide are suspended in 120g of methyl acetate in the apparatus described in Example 1 and 210g of hydrogen bromide are introduced into this suspension at a temperature below 40°C. Subsequently and at a temperature below 50°C, 91g of propylene oxide are added in doses. From the reaction mixture, 45g of methyl acetate are then distilled off in the rotation evaporator. Subsequently the mixture is cooled in an ice bath, whereby the β-bromoisobutyric amide formed crystallizes out. It is filtered off, washed with a little methyl acetate and dried. The yield amounts to 117g corresponding to 70.5% of the theory. The melting point lies between 95° and 102°C.

We claim:
1. Process for the production of halogenated carboxylic acid amides, comprising reacting an amide of an unsaturated aliphatic carboxylic acid with an anhydrous hydrogen halide, adding an epoxide compound to the reaction mixture, and after cooling, separating the precipitated halogenated carboxylic acid amide.

2. Process as recited in claim 1, wherein the amide of the unsaturated aliphatic carboxylic acid is used, dissolved or suspended in an organic solvent.

3. Process as recited in claim 1, wherein an amide of an α-β-unsaturated carboxylic acid is used as said amide of an unsaturated aliphatic carboxylic acid.

4. Process as recited in claim 1, wherein said epoxide compound has 2 to 4 C atoms in the molecule.

5. Process as recited in claim 1, wherein an epihalogenated hydrine is used as said epoxide compound.

6. Process as recited in claim 1, wherein during the conversion of the amide of the unsaturated aliphatic carboxylic acid with the anhydrous hydrogen halide, a temperature of 20° to 50°C is maintained in the reaction mix.

7. Process as recited in claim 1, wherein during the addition of the epoxide compound, a temperature of 20° to 50°C is maintained in the reaction mix.

8. Process as recited in claim 1, wherein the reaction mix is cooled to a temperature of 10° to 20°C prior to the separation of the halogenated carboxylic acid amide.

9. Process as recited in claim 1, wherein anhydrous hydrogen bromide is introduced into a solvent or suspension of acrylic amide in an organic solvent and from the reaction product developing, 3-bromopropionic amide is separated by the addition of an alkylene oxide or of an epihalogenated compound, and that said separation is effected after cooling of the reaction mixture.

* * * * *